United States Patent [19]

Komiyama et al.

[11] Patent Number: 4,804,412

[45] Date of Patent: Feb. 14, 1989

[54] DENTURE ADHESIVE

[75] Inventors: Noboru Komiyama, Tokyo; Masayuki Oguma, Chiba; Noriko Miyamoto, Ichikawa, all of Japan

[73] Assignee: Lion Corporation, Japan

[21] Appl. No.: 43,535

[22] Filed: Apr. 28, 1987

[30] Foreign Application Priority Data

May 13, 1986 [JP] Japan ................................. 61-109028

[51] Int. Cl.$^4$ ........................ A61C 13/23; A61K 6/00; C09J 3/14; C09J 3/26

[52] U.S. Cl. ..................................... 106/35; 106/208; 433/168.1; 433/180; 523/118; 523/120; 524/110; 524/111; 524/310; 524/317; 524/376; 524/377; 524/563

[58] Field of Search ................... 106/35, 208; 523/118, 523/120, 121; 426/6; 433/168.1, 180; 524/110, 111, 310, 317, 376, 377, 563

[56] References Cited

U.S. PATENT DOCUMENTS

| | | | |
|---|---|---|---|
| 3,285,750 | 11/1966 | Ishida | 426/6 |
| 3,396,038 | 8/1968 | Knapp | 426/6 |
| 4,001,151 | 1/1977 | Keegan et al. | 523/120 |
| 4,073,756 | 2/1978 | Yotsuyanagi et al. | 106/211 |
| 4,088,500 | 5/1978 | Fairbanks et al. | 106/35 |
| 4,318,742 | 3/1982 | Lokken | 106/35 |

FOREIGN PATENT DOCUMENTS 023812 6/1974 Japan .
031435 2/1986 Japan .

Primary Examiner—Paul Lieberman
Assistant Examiner—Linda D. Skaling
Attorney, Agent, or Firm—Lorusso & Loud

[57] ABSTRACT

A denture adhesive composition which has improved removability from denture plates and easiness in being squeezed out of a tube and which includes a low softening-point resin selected from polyvinyl acetate resins and natural chicles, and at least one compound having a molecular weight of about 120–7000 and containing one or more polyoxypropylene groups of the formula $-(CH_2-CHCH_3-O)_{\overline{n}}$ where n is an integer of 2–120 in an amount of at least 60% of the molecular weight of the compound.

2 Claims, No Drawings

DENTURE ADHESIVE

This invention relates to a denture adhesive.

A denture becomes less and less stable on the gums with a passage of time because the gums tend to wither, thus giving rise to the difficulty in maintaining comfortable denture fit. To cope with this problem, denture adhesives have been developed and are now increasingly used. There are available two types of denture adhesives in commerce, one being of the adhesion type using a water-soluble polymer as a base material and the other being of the cushioning type using a low softening point resin such as polyvinyl acetate as a base material. Although the denture adhesive of the cushioning type is more advantageous than that of its adhesion type in terms of the effectiveness to hold dentures, it still has defects because it is difficult to squeeze out from a tube so that it is inconvenient to spread over a denture plate and because it is difficult to remove from the denture plate so that a difficulty is encountered when it is renewed after use.

The present invention has been made in consideration of the above-described problems of the conventional denture adhesives.

In accordance with the present invention, there is provided a composition of matter, comprising:
a low softening-point resin selected from the group consisting of polyvinyl acetate resins, chicles and mixtures thereof; and
at least one compound containing one or more polyoxypropylene groups of the formula $-CH_2-CHCH_3-O)_{n}$ where n is an integer of 2-120 and having a molecular weight of about 120-7000, said one or more groups accounting for at least 60% of the molecular of said compound.

A low-softening point resin selected from polyvinyl acetates, natural chicles and mixtures thereof is used as a base material for the denture adhesive according to the present invention. Preferably, the low-softening point resin has an average polymerization degree of 200-1200.

The denture adhesive further includes at least one compound containing one or more polyoxypropylene groups of the formula $-(CH_3-CHCH_3-O)_{n}$ where n is an integer of 2-200 and having a molecular weight of 120-7000, at least 60% of which is attributed to the one or more polyoxypropylene groups.

Examples of such compounds include homopolymers of propylene oxide, copolymers of propylene oxide and ethylene oxide and addition products obtained by addition-polymerizing propylene oxide or propylene oxide and ethylene oxide with a monovalent or polyvalent alcohol or a monobasic or polybasic carboxylic acid.

In preparing the above-described addition products, the order of the addition of the monomers is optional, i.e. the addition of propylene oxide may be preceded or followed by the addition of ethylene oxide. It is also possible to react these monomers simultaneously with a monovalent or polyvalent alcohol or a monobasic or polybasic carboxylic acid.

The monovalent alcohol to be used for the preparation of the addition products may include, for example, a saturated alcohol such as methanol, ethanol, propanol (n- and iso-), butanol (n-, iso-, sec- and tert-), pentanol, pentanol-1, pentanol-2, pentanol-3, 2-methylbutanol-1, 2-methylbutanol-2, 2-methylbutanol-3, 2-methylbutanol-4, dimethylpropanol, hexanol-1, hexanol-2, heptanol-1, heptanol-2, octanol-1, octanol-2, 4-ethylhexanol-4, 2-ethylhexanol-1, nonanol-1, nonanol-2, nonanol-3, decanol-1, decanol-2, undecanol-1, undecanol-2, dodecanol-1 and dodecanol-2, and an unsaturated alcohol such as allyl alcohol, crotyl alcohol, 2-butenol-1, 2-pentenol-1, 3-hexenol-1, 2-heptenol-1, 10-undecenol-1, 11-dodecenol-1, 12-tridecenol-1 and oleyl alcohol.

The polyvalent alcohol to be used for the preparation of the addition products may include, for example, ethylene glycol, polyethylene glycol, propylene glycol, butylene glycol, glycerine, polyglyceride, batyl alcohol, pentaerythritol, xylitol, sorbitol, a monosaccharide such as mannitol, maltitol and glucose, a disaccharide such as sucrose and lactose, and a polysaccharide such as cellulose.

As the monobasic carboxylic acids may be illustrated, for example, a saturated acid such as formic acid, acetic acid, propionic acid, butyric acid, valeric acid, caproic acid, enanic acid, caprylic acid, pelargonic acid, capric acid, undecylenic acid, lauric acid, tridecanoic acid, meristic acid, pentadecanoic acid, palmitic acid and stearic acid, and an unsaturated acid such as crotonic acid, isocrotonic acid, 2-hexenoic acid, 4-decenoic acid, 9-decenoic acid, 3-dodecenoic acid, 5-dodecenoic acid, and 11-dodecenoic acid.

The polybasic carboxylic acids may include, for example, a straight saturated dibasic acid such as oxalic acid, malonic acid, succinic acid, glutaric acid, adipic acid, pimelic acid, suberic acid, azelaic acid, sebacic acid and 1,9-nonamethylene carboxylic acid.

In accordance with the present invention, there may be used a fatty acid such as sorbic acid, linoleic acid and linolenic acid and a mineral acid such as phosphoric acid, in addition to those acids as have been described above.

The OH residues of the polybasic carboxylic acids, which are not participated in the addition of propylene oxide or ethylene oxide may be converted into a metal salt with an alkali metal or alkaline earth metal such as $Li^+$, $K^+$, $Na^+$, $Ca^{++}$ and $Mg^{++}$ or into a salt of $NH_4^+$. The terminal end or ends of the above-described compounds to be added to the denture adhesive according to the present invention may be in the form of a hydroxyl group, an ether group with a monovalent or polyvalent alcohol, an ester group with a monobasic or polybasic carboxylic acid or a salt thereof. The terminal end group or groups may be the monovalent or polyvalent alcohol or the monobasic or polybasic carboxylic acid employed at the time of starting the addition polymerization with propylene oxide or ethylene oxide.

As described above, the polymerization degree of the propylene oxide in the polyoxypropylene group of the compound to be added in the denture adhesive should be 2 to 120. A polymerization degree of less than 2 causes an increase of hydrophilicity of the compound to the extent that the removability of the denture adhesive from the denture plates becomes poor. On the other hand, too high a polymerization degree in excess of 120 impairs the safety to human body due to possible increase of formyl or carbonyl groups in the compound. The content of the polyoxypropylene group or groups in the compound should be such as to account for at least 60% of the molecular weight thereof in order for the denture adhesive to have optimum hydrophilic properties.

The amount of the polypropylene oxide-containing compound to be formulated in accordance with the present invention may be in the range of from 0.1 to 30% by weight, preferably from 0.5% to 10% by weight. If the amount of the compound is less than 0.1% by weight, a removability of the denture adhesive from denture plates is rendered insufficient. If the amount of the compound is more than 30% by weight, on the other hand, the low-softening point resin used as the base material of the denture adhesive gets softened too much, thereby leading to a reduction of cushioning properties.

The denture adhesive in accordance with the present invention may further include other ingredients such as non-toxic fats, oils, waxes, emulsifiers, water-insoluble powders, enzymes, water, ethanol, pigments and so on, if desired. The non-toxic fats, oils and waxes may include, for example, bees wax, haze wax, condelilla wax, microcrystalline wax, paraffin wax and carnauba wax. The emulsifiers may include, for example, stearic acid monoglyceride, oleic acid monoglyceride, a fatty acid acetylglyceryl ester such as acetylglyceryl monostearate or sorbitan monostearate. The water-insoluble powders may include, for example, calcium carbonate, calcium hydrogen phosphate, silica, zeolite, plastic powder and cellulose powder. The enzymes may include, for example, dextranase, mutanase, levanase and inulinase.

The denture adhesive according to the present invention exhibits good cushioning properties, ease in being squeezed out from a tube and a good removability from denture plate and, therefore, is very suited for practical use. Although reasons why the denture adhesive according to the present invention provides such effects as described above are not clear, it is assumed that the ease by which it is squeezed out from a tube and its removability from denture plates are attributable to the good compatibility of the polyoxypropylene-containing compound with the low softening point resin which exhibits suitable cushioning properties and wich is hydrophilic in nature and to the hydrophobic properties of the polyoxypropylene-containing compound which serves to reduce the hydrophibilicity of the low softening point resin.

The following examples will further illustrate the present invention.

EXAMPLES 1-27 AND COMPARATIVE EXAMPLES 1-4

Using the ingredients shown in Table below in the proportions (% by weight, balance being distilled water) shown in the Table, various denture adhesives were prepared. The ease with which the denture adhesives may be squeezed out from a tube and removability of the denture adhesives from denture plates were tested in the manner described below. The results are also shown in the Table below.

Easiness in Squeezed Out

Each of the denture adhesives under test was filled in an aluminum tube. The easiness in squeezing-out was measured in terms of pressure (kg/g) required for squeezing out 1 gram of the test sample from the tube at a temperature of 20° C. It is thus to be understood that the smaller the figure, the easier is the squeezing-out.

Removability:

Each of the denture adhesives was spread on each denture plates of five upper full dentures. The dentures were then set in months. After practical use for 24 hours, the denture adhesives were removed from the plates by hands at 25° C. Average times required for the removal were measured. The removability is rated as follows:

A: Average time of less than 5 minutes
B: Average time of 5–10 minutes
C: Average time of 10–20 minutes
D: Average time of more than 20 minutes In the Table:
*1: Polypropylene oxide (average molecular weight (amw) 4000)
*2: Polypropylene oxide (amw 2000)
*3: Polypropylene oxide (amw 200)
*4: Polyoxypropylene glyceryl ether (amw 3000)
*5: Polyoxypropylene mannitol ether (amw 750)
*6: Acetic acid ester of SANNIX PP-200 (amw 250)
*7: Polyoxypropylene butyl ether (amw 1400)
*8: Polyoxypropylene butyl ether (amw 3000)
*9: Polyoxyethylene/polyoxypropylene glycol copolymer (amw 3600, content of polyoxypropylene glycol: 90 wt %)
*10: Polyoxyethylene/polyoxypropylene glycol copolymer (amw 3000, content of polyoxypropylene glycol: 60 wt %)
*11: Polyoxyethylene/polyoxypropylene glycol copolymer (amw 8750, content of polyoxypropylene glycol: 20 wt %)
*12: Polyoxyethylene(1)polyoxypropylene(8) cetyl ether
*1–*6: Trademarks of Sanyo Kasei Kogyo K.K.
*7–*8: Trademarks of Nihon Yushi K.K.
*9–11: Trademarks of Asahi Denka Kogyo K.K.
*12: Trademark of Nippon Chemicals K.K.

TABLE

| | Example | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Polyvinyl acetate | 50 | 50 | 50 | 50 | 50 | 50 | 50 | 50 | 50 | 50 | 50 | — | — | — | 60 | 60 | 60 |
| Natural chicle | — | — | — | — | — | — | — | — | — | — | — | 50 | 50 | 50 | — | — | — |
| Stearic acid monoglyceride | 2 | 2 | 2 | 2 | 2 | 2 | 2 | 2 | 2 | 2 | 2 | 2 | 2 | 2 | 3 | 3 | 3 |
| Bleached bees wax | — | — | — | — | — | — | — | — | — | — | — | — | — | — | — | — | — |
| Calcium carbonate | 7 | 7 | 7 | 7 | 7 | 7 | 7 | 7 | 7 | 7 | 7 | 7 | 7 | 7 | — | — | — |
| Ethanol | 20 | 20 | 20 | 20 | 20 | 20 | 20 | 20 | 20 | 20 | 20 | 20 | 20 | 20 | 20 | 20 | 20 |
| SANNIX PP-4000 *1 | 3 | — | — | — | — | — | — | — | — | — | — | 3 | — | — | 3 | — | — |
| SANNIX PP-2000 *2 | — | 3 | — | — | — | — | — | — | — | — | — | — | 3 | — | — | 3 | — |
| SANNIX PP-200 *3 | — | — | 3 | — | — | — | — | — | — | — | — | — | — | 3 | — | — | 3 |
| SANNIX GP-3000 *4 | — | — | — | 3 | — | — | — | — | — | — | — | — | — | — | — | — | — |
| SANNIX SP-750 *5 | — | — | — | — | 3 | — | — | — | — | — | — | — | — | — | — | — | — |
| SANNIX PP-200 *6 acetic ester | — | — | — | — | — | 3 | — | — | — | — | — | — | — | — | — | — | — |
| UNILUBE MB-22 *7 | — | — | — | — | — | — | 3 | — | — | — | — | — | — | — | — | — | — |
| UNILUBE MB-700 *8 | — | — | — | — | — | — | — | 3 | — | — | — | — | — | — | — | — | — |
| PLURONIC L-101 *9 | — | — | — | — | — | — | — | — | 3 | — | — | — | — | — | — | — | — |
| PLURONIC L-64 *10 | — | — | — | — | — | — | — | — | — | 3 | — | — | — | — | — | — | — |

TABLE-continued

| | | | | | | | | | | | | | | | | |
|---|---|---|---|---|---|---|---|---|---|---|---|---|---|---|---|---|
| PLURONIC F-68 *11 | — | — | — | — | — | — | — | — | — | — | — | — | — | — | — | — |
| NIKKOL PBC-41 *12 | — | — | — | — | — | — | — | — | — | — | 3 | — | — | — | — | — |
| Easiness in squeezing out | 4.8 | 3.6 | 2.2 | 4.5 | 3.4 | 4.9 | 3.3 | 3.6 | 3.3 | 4.1 | 5.3 | 7.5 | 6.3 | 3.9 | 5.4 | 4.4 | 3.8 |
| Removability | A | A | B | A | B | B | B | A | A | B | C | A | A | A | A | A | B |

| | Example | | | | | | | | | | Comptv. Example | | | |
|---|---|---|---|---|---|---|---|---|---|---|---|---|---|---|
| | 18 | 19 | 20 | 21 | 22 | 23 | 24 | 25 | 26 | 27 | 1 | 2 | 3 | 4 |
| Polyvinyl acetate | 60 | 60 | 55 | 50 | 40 | 50 | 50 | 50 | 50 | 50 | 50 | 60 | — | — |
| Natural chicle | — | — | 5 | 10 | 20 | — | — | — | — | 10 | — | — | 50 | 60 |
| Stearic acid monoglyceride | 3 | 3 | 1 | 1 | 2 | 2 | 2 | 2 | 2 | 2 | 2 | 3 | 2 | 3 |
| Bleached bees wax | — | — | — | — | — | 1 | 1 | 1 | 1 | 1 | 3 | — | 3 | — |
| Calcium carbonate | — | — | — | — | — | 7 | 5 | 5 | 5 | 5 | 7 | — | 7 | — |
| Ethanol | 20 | 20 | 20 | 20 | 20 | 15 | 15 | 15 | 20 | 20 | 20 | 20 | 20 | 20 |
| SANNIX PP-4000 *1 | — | — | 5 | — | — | — | — | — | — | — | — | — | — | — |
| SANNIX PP-2000 *2 | — | — | — | 5 | 5 | 0.5 | 10 | 15 | — | — | — | — | — | — |
| SANNIX PP-200 *3 | — | — | — | — | — | — | — | — | — | — | — | — | — | — |
| SANNIX GP-3000 *4 | 3 | — | — | — | — | — | — | — | — | — | — | — | — | — |
| SANNIX SP-750 *5 | — | — | — | — | — | — | — | — | — | — | — | — | — | — |
| SANNIX PP-200 *6 acetic ester | — | — | — | — | — | — | — | — | — | — | — | — | — | — |
| UNILUBE MB-22 *7 | — | — | — | — | — | — | — | — | — | — | — | — | — | — |
| UNILUBE MB-700 *8 | — | 3 | — | — | — | — | — | — | 3 | 3 | — | — | — | — |
| PLURONIC L-101 *9 | — | — | — | — | — | — | — | — | 2 | 2 | — | — | — | — |
| PLURONIC L-64 *10 | — | — | — | — | — | — | — | — | — | — | — | — | — | — |
| PLURONIC F-68 *11 | — | — | — | — | — | — | — | — | — | — | — | 3 | — | 3 |
| NIKKOL PBC-41 *12 | — | — | — | — | — | — | — | — | — | — | — | — | — | — |
| Easiness in squeezing out | 4.1 | 4.2 | 5.7 | 5.9 | 6.3 | 8.2 | 2.9 | 2.5 | 3.4 | 3.3 | 10.6 | 13.3 | 15.7 | 16.0 |
| Removability | A | A | B | B | B | B | A | A | A | A | D | D | D | D |

We claim:

1. A denture adhesive composition consisting essentially of:
   a low softening-point resin selected from the group consisting of polyvinyl acetate resins, chicles and mixtures thereof; and
   at least one compound containing one or more polypropylene groups of the formula $+CH_2-CHCH_3+O)_n$ where n is an integer of 2–120 and having a molecular weight of about 120–7000, said one or more groups accounting for at least 60% of the molecular weight of said compound,
   said at least one compound being selected from the group consisting of:
   (1) homopolymers of propylene oxide,
   (2) copolymers of propylene oxide and ethylene oxide and
   (3) products obtained by addition polymerizing propylene oxide or propylene oxide and ethylene oxide with
   (a) a monovalent alcohol selected from methanol, ethanol, n-propanol, isopropanol, n-butanol, isobutanol, sec-butanol, tert-butanol, pentanol, pentanol-1, pentanol-2, pentanol-3, 2-methylbutanol-1, 2-methylbutanol-2, 2-methylbutanol-3, 2-methylbutanol-4, dimethylpropanol, hexanol-1, hexanol-2, heptanol-1, heptanol-2, octanol-1, octanol-2, 4-ethylhexanol-4, 2-ethylhexanol-1, nonanol-1, nonanol-2, nonanol-3, decanol-1, decanol-2, allyl alcohol, crotyl alcohol, 2-butenol-1, 2-pentenol-1, 3-hexenol-1, and 2-heptenol-1,
   (b) a polyvalent alcohol selected from ethylene glycol, propylene glycol, butylene glycol, glycerine, pentaerythritol, xylitol, sorbitol, mannitol, maltitol, glucose and lactose,
   (c) a monobasic carboxylic acid selected from formic acid, acetic acid, propionic acid, butyric acid, valeric acid, caprocic acid, enanic acid, caprylic acid, pelargonic acid, capric acid, crotonic acid, isocrotonic acid, 2-hexenoic acid, 4-decenoic acid and 9-decenoic acid, or
   (d) a polybasic carboxylic acid selected from oxalic acid, malonic acid, succinic acid, glutaric acid, adipic acid, pimelic acid, suberic acid, azelaic acid, sebacic acid and 1,9-nonamethylene carboxylic acid,
   the content of said at least one compound in said composition being 0.1 to 30% by weight.

2. A composition as claimed in claim 1, wherein said polyvinyl acetate resins have an average polymerization degree of 200–1200.

* * * * *

UNITED STATES PATENT AND TRADEMARK OFFICE
CERTIFICATE OF CORRECTION

PATENT NO. : 4,804,412

DATED : February 14, 1989

INVENTOR(S) : KOMIYAMA et al

It is certified that error appears in the above-identified patent and that said Letters Patent is hereby corrected as shown below:

Column 1, line 6, delete the "a";

line 7, after "maintaining" insert --a--;

line 17, "the" should read --its--; and line 45, "$-(-CH_3-CHCH_3-O-)_n-$" should read $-(-CH_2-CHCH_3-O-)_n-$.

Column 3, line 38, "wich" should read --which--.
Column 6, line 40, "caprocic" should read --caproic--.

Signed and Sealed this

Twenty-third Day of January, 1990

Attest:

JEFFREY M. SAMUELS

*Attesting Officer*  *Acting Commissioner of Patents and Trademarks*